United States Patent [19]

Guglielmetti

[11] Patent Number: 4,539,161
[45] Date of Patent: Sep. 3, 1985

[54] AMINE OXIDE COMPOUNDS

[75] Inventor: Leonardo Guglielmetti, Bottmingen, Switzerland

[73] Assignee: Ciba Geigy Corporation, Ardsley, N.Y.

[21] Appl. No.: 282,559

[22] Filed: Jul. 13, 1981

[30] Foreign Application Priority Data

Jul. 25, 1980 [CH] Switzerland .................. 5708/80

[51] Int. Cl.³ .................. C07C 121/66; C07C 135/02
[52] U.S. Cl. .................. 260/465 E; 564/156;
564/180; 564/299; 564/83; 564/84; 564/85;
564/86; 564/88; 564/89; 564/153; 564/154;
544/219; 548/255; 548/256; 548/378; 548/379;
260/465 D; 260/456 A; 260/505 C; 560/8;
560/88; 560/102; 562/442
[58] Field of Search .................. 564/83, 84, 85, 86,
564/88, 89, 153, 154, 156, 180, 299; 252/301.21,
301.22; 260/465 D, 465 E, 456 A, 505 C; 560/8,
88, 102; 562/442

[56] References Cited

U.S. PATENT DOCUMENTS

| | | | |
|---|---|---|---|
| 3,135,745 | 6/1964 | Palopole et al. | 564/299 |
| 3,206,512 | 9/1965 | Koehner et al. | 260/560.7 |
| 3,293,247 | 12/1966 | Duennenberger et al. | 260/248 |
| 3,453,262 | 7/1969 | Roberts et al. | 252/301.22 |
| 3,494,962 | 2/1970 | Miller et al. | 260/570.8 |
| 3,963,649 | 6/1976 | Spadini et al. | 252/546 |
| 4,172,045 | 10/1979 | Meyer et al. | 252/301.22 |
| 4,276,188 | 6/1981 | Meyer | 252/301.22 |

Primary Examiner—Henry R. Jiles
Assistant Examiner—Bernard I. Dentz
Attorney, Agent, or Firm—Edward McC. Roberts; Kevin T. Mansfield

[57] ABSTRACT

Novel amine oxide compounds of the formula

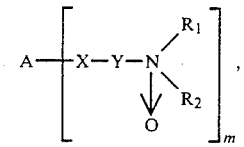

in which m is the integer 1 or 2, A is a through-conjugated radical of a fluorescent brightener system, which radical contains unsubstituted or non-chromophorically substituted aromatic carbocyclic and/or heterocyclic rings, X is a direct bond between A and Y, an oxygen atom or sulfur atom or a group of the formula $-SO_2-$, $-SO_2-O-$, $-COO-$, $-CON(R)-$ or $-SO_2N(R)-$, in which R is hydrogen or unsubstituted or non-chromophorically substituted alkyl, Y is an unsubstituted or non-chromophorically substituted straight-chain or branched alkylene or alkyleneoxyalkylene group, and $R_1$ and $R_2$ independently of one another are cycloalkyl, unsubstituted or non-chromophorically substituted alkyl or phenyl, or $R_1$ and $R_2$, together with the nitrogen atom to which they are bonded, are a 5-membered or 6-membered saturated or unsaturated heterocyclic ring which can additionally contain one or two further hetero-atoms as ring members, and which can be substituted further, or, if X is a group of the formula $-CON(R)-$ or $-SO_2N(R)-$ and Y is ethylene or propylene, R and $R_1$ together are an ethylene or methylene group, thereby forming a corresponding saturated heterocyclic ring containing 2 nitrogen atoms.

The novel amine oxide compounds can be prepared, for example, by oxidizing the corresponding amino compounds with per-compounds. They can be used as fluorescent brighteners, especially for brightening cellulose in a washing liquor. The brighteners exhibit particularly advantageous properties when used in liquid detergents containing cationic textile softeners.

6 Claims, No Drawings

AMINE OXIDE COMPOUNDS

The present invention relates to novel amine oxide compounds, processes for their preparation, their use as fluorescent brighteners, preferably in detergents containing cationic textile treatment agents, and detergents, textile treatment agents and laundry after-treatment agents containing the novel compounds.

Previously known fluorescent brighteners which contain a N-oxide group are in every case derivatives of v-triazole-N-oxide; compare, for example, British Patent Specification 1,190,511 and German Offenlegungsschrift No. 1,906,662. In most cases, the v-triazole-N-oxide compounds have only been described as intermediates for the preparation of fluorescent brighteners containing a v-triazole group, for example in British Patent Specifications Nos. 1,190,512 and 1,190,514, U.S. Patent Specification No. 3,819,645, Swiss Patent Specifications Nos. 551,987, 561,707 and 561,709 and German Offenlegungsschrift No. 2,712,408.

The known N-oxides of v-triazolyl brighteners have the disadvantage that the strongly semi-polar N-oxide bond is present directly in the conjugated brightener system. This results in partial annulment of the conjugation of the system, which also produces a reduction of the brightening effect.

It was the object of the present invention to provide novel fluorescent brighteners which on the one hand have the advantages of the strongly semi-polar N-oxide bond (high dipole moment and accordingly a zwitter-ion character of the compounds), without possessing the disadvantages of the known N-oxide brighteners described above, and which possess excellent applicational properties.

In particular, it was also an object of the invention to provide fluorescent brighteners which, in washing agents, are not only compatible with anionic detergents but also with cationic surfactants, textile softeners and other cationic textile assistants, especially in an acid medium. In acid solutions, the amine oxides according to the invention form quaternary ammonium ions and accordingly also possess cationic properties.

Compared to known cationic brighteners, for example those which contain a quaternary ammonium group, the amine oxide brighteners according to the invention have the advantage that they can, in a neutral and alkaline medium, also function as non-ionic brighteners (through formation of the non-ionic hydrates) and that accordingly they have a broader spectrum of applications. They can also be employed together with anionic detergents in conventional washing agents. Furthermore, they exhibit greater soiling resistance, especially against sebum soiling (soiling resulting from skin secretions), than known brighteners which are usable in washing agents containing cationic textile treatment agents.

Surprisingly, it has proved possible to achieve the objects described above through providing the brighteners according to the invention, which possess an amine oxide group, separate from the conjugated system of the brightener, in one or two substituents.

The novel brighteners according to the invention are amine oxide compounds of the formula

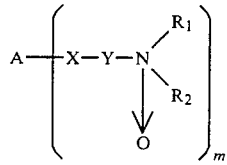
(1)

in which m is the integer 1 or 2, A is a through-conjugated radical of a fluorescent brightener system, which radical contains unsubstituted or non-chromophorically substituted aromatic carbocyclic and/or heterocyclic rings, X is a direct bond between A and Y, an oxygen atom or sulfur atom or a group of the formula $-SO_2-$, $-SO_2-O-$, $-COO-$, $-CON(R)-$ or $-SO_2N(R)-$, in which R is hydrogen or unsubstituted or non-chromophorically substituted alkyl, Y is an unsubstituted or non-chromophorically substituted straight-chain or branched alkylene or alkyleneoxyalkylene group, and $R_1$ and $R_2$ independently of one another are cycloalkyl, unsubstituted or non-chromophorically substituted alkyl or phenyl, or $R_1$ and $R_2$, together with the nitrogen atom to which they are bonded, are a 5-membered or 6-membered saturated or unsaturated hetercyclic ring which can additionally contain one or two further hetero-atoms as ring members, and which can be substituted further, or, if X is a group of the formula $-CON(R)-$ or $-SO_2N(R)-$ and Y is ethylene or propylene, R and $R_1$ together are an ethylene or methylene group, thereby forming a corresponding saturated heterocyclic ring containing 2 nitrogen atoms.

A, as the radical of a brightener system, can be any desired skeleton which is known in the chemistry of fluorescent brighteners, possesses a conjugated system of double bonds and contains aromatic carbocyclic and/or heterocyclic rings in a known arrangement.

Specific examples of brightener radicals A are those from the group of the 2-furanyl-benzimidazoles, 2-azolyl-benzimidazoles, 2-stilbenyl-benzoxazoles, 2-stilbenyl-benzimidazoles, 1,2-bis-azolylethylenes, 2,5-bis-benzimidazolylfurans, 4,4'-bis-azolylstilbenes, 2-phenyl-5-azolyl-thiophenes, 1,3-diphenylpyrazolines, 4,4'-distyryl-biphenyls, 4,4'-divinyl-stilbenes, 1,4-distyrylbenzenes, 3,7-disubstituted coumarins, naphthalimides, 2-stilben-4-yl-naphthotriazoles, 4,4'-bis-triazolyl-stilbenes, 4,4'-bis-pyrazolyl-stilbenes, triazolyl-stilbenes, pyrazolyl-stilbenes, naphthotriazolyl-stilbenes, triazinylpyrenes and bis-styryl-dibenzofurans.

The basic structures of the brightener radicals A can be unsubstituted or can carry non-chromophoric substituents known from the chemistry of fluorescent brighteners. Examples of such substituents are halogen, alkyl, hydroxyalkyl, halogenoalkyl, cyanoalkyl, alkoxyalkyl, phenylalkyl, carboxyalkyl, carbalkoxyalkyl, alkenyl, cycloalkyl, alkoxy, alkenyloxy, alkoxycarbonyl, aminocarbonyl, alkylaminocarbonyl, dialkylaminocarbonyl, cyano, alkylsulfonyl, alkoxysulfonyl, aminosulfonyl, hydroxyl, carboxyl, sulfo and trifluoromethyl. In the above substituents, alkyl and alkoxy groups, also in composite groups, for example alkoxyalkyl, each individually have, for example, 1 to 10, preferably 1 to 6, especially 1 to 4, carbon atoms. Cycloalkyl preferably has 5 or 6 carbon atoms and alkenyl in particular has 3 or 4 carbon atoms. Amongst the halogen atoms, fluorine, chlorine and bromine, especially chlorine, are preferred. The number of possible substituents of the above type depends on the basic structure of the brightener system and also on the particular substituents but can be from 1 to 4. Preferably, 1 or 2 such substituents are present.

Preferred substituents of this type are, for example, halogen atoms (especially chlorine), $C_1$-$C_4$-alkyl, cyclohexyl, $C_3$-$C_4$-alkenyl, $C_1$-$C_4$-alkoxy, $C_3$-$C_4$-alkenyloxy, phenylsulfonyl, $C_1$-$C_4$-alkylsulfonyl, $C_2$-$C_5$-carbalkoxy, carbamoyl and sulfamoyl groups, the amide group being unsubstituted or substituted by 1 or 2 groups chosen from $C_1$-$C_4$-alkyl, $C_1$-$C_4$-hydroxyalkyl, $C_2$-$C_5$-cyanoalkyl, $C_1$-$C_4$-halogenoalkyl, benzyl or phenyl, or the amide group being a saturated 5-membered or 6-membered nitrogen-containing heterocyclic radical, for example a piperidine, piperazine, morpholine, pyrrolidine, imidazolidine or thiomorpholine radical, which can be substituted by one or 2 alkyl or hydroxyalkyl groups.

Non-chromophoric substituents of alkyl groups R, $R_1$ and $R_2$ or of the alkylene or alkyleneoxyalkylene group Y are, for example, halogen (especially chlorine), hydroxyl, $C_2$-$C_5$-carbalkoxy, $C_1$-$C_4$-alkoxy, phenyl, chlorophenyl, methylphenyl, methoxyphenyl, carbamoyl or sulfamoyl (possible substituents of the amide groups being as in the preceding paragraph).

Preferred substituted alkyl groups are chloroalkyl, hydroxyalkyl, cyanoalkyl, phenylalkyl (especially benzyl) and alkoxyalkyl.

Particular examples of 5-membered or 6-membered saturated heterocyclic rings which can be formed by $R_1$ and $R_2$ together with the nitrogen atom are the piperidine, piperazine, morpholine, thiomorpholine, pyrrolidine and imidazolidine ring, and these can additionally be substituted, for example by one or 2 alkyl groups having 1 to 4 carbon atoms.

Particular examples of 5-membered or 6-membered unsaturated heterocyclic rings which $R_1$ and $R_2$ can form conjointly with the nitrogen atom are pyrrolyl, imidazolyl, pyrazolyl, 1,2,3-triazolyl, 1,2,4-triazolyl, tetrazolyl, benzimidazolyl and benztriazolyl radicals, which can be substituted, for example by halogen atoms such as chlorine or bromine, or by unsubstituted or substituted alkyl groups or alkoxy groups (in each case preferably having 1–4 carbon atoms). Examples are pyrazol-1-yl, 4-methylpyrazol-1-yl, 3,5-dimethylpyrazol-1-yl, 4-methoxypyrazol-1-yl, 4-methoxy-ethoxypyrazol-1-yl, imidazol-1-yl, 2-methylimidazol-1-yl, benzimidazol-1-yl, 1,2,3-triazol-1-yl, benztriazol-1-yl, 1,2,4-triazol-1-yl, 3,5-dimethyl-1,2,4-triazol-1-yl and 1,2,3,4-tetrazol-1-yl radicals.

The alkylene or alkyleneoxyalkylene group Y can be branched or straight-chain and can, for example, have 1 to 20 carbon atoms. Preferably, it contains 1 to 12, especially 1 to 6, carbon atoms. Unbranched alkylene groups with 1 to 4 carbon atoms are particularly preferred.

If X is —CON(R)— or —$SO_2$N(R)— and Y is ethylene or propylene, R and $R_1$ can conjointly be ethylene or methylene. This gives groups of the formula

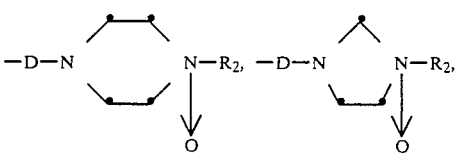

-continued

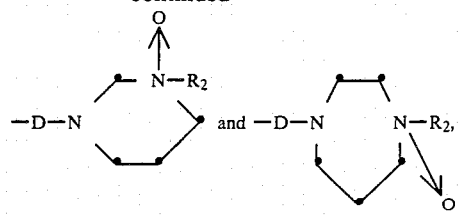

of which the first three are preferred and the first is particularly preferred. D is in each case CO or $SO_2$.

Preferred amine oxide compounds are those of the formula (1), in which X is an oxygen atom or sulfur atom or a group of the formula —$SO_2$—, —CON(R)— or —$SO_2$N(R)— and Y is a straight-chain or branched alkylene group having 1 to 12 carbon atoms, R being as defined under formula (1) or R and $R_1$ together being as defined under formula (1).

Amongst the compounds of the formula (1), amine oxide compounds which are particularly important in practice are those of the formula

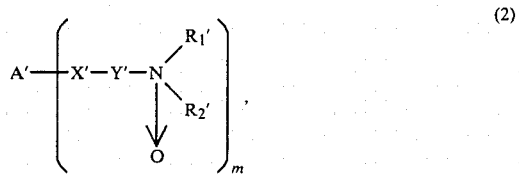

in which A' is an unsubstituted or non-chromophorically substituted radical of the formula (3)

(4)

(5)

(6)

(7)

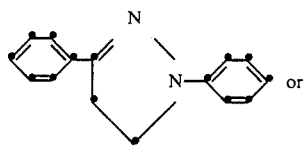

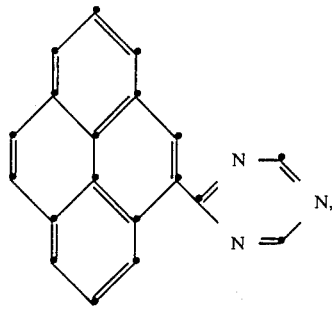

X' is an oxygen atom or a group of the formula —SO₂N(R')— or —SO₂—, R' being hydrogen or alkyl, having 1 to 4 carbon atoms, which is unsubstituted or substituted by hydroxyl, cyano or halogen, Y' is a straight-chain or branched alkylene or alkyleneoxyalkylene group, m is the integer 1 or 2 and $R_1'$ and $R_2'$ independently of one another are alkyl having 1 to 8 carbon atoms, which is unsubstituted or substituted by halogen, cyano, hydroxyl, alkoxy having 1 to 4 carbon atoms, phenyl, chlorophenyl, methoxyphenyl, methylphenyl or alkoxycarbonyl having 2 to 5 carbon atoms, or $R_1'$ and $R_2'$ together with the nitrogen atom to which they are bonded are a 5-membered or 6-membered saturated or unsaturated heterocyclic ring which can contain one or two further hetero-atoms as ring members, and which can be substituted further, and, if X' is a group of the formula —SO₂N(R')— and Y' is ethylene or propylene, R' and $R_1'$ together can be ethylene or methylene, thereby producing a group of the formula

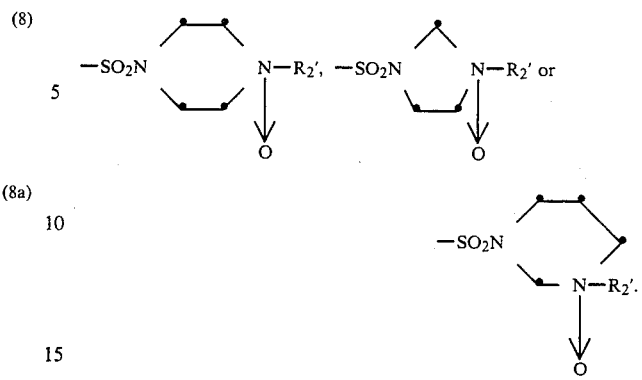

The brightener radicals of the formulae (3) to (8a) can be unsubstituted or can, for example, contain the substituents mentioned initially for the group A. Preferably, the radicals of the formulae (3) and (4) have 2 substituents, which as a rule are identical and preferably are arranged symmetrically, especially on the outer phenyl rings. The other radicals, if they are substituted, preferably contain 1 or 2 of the substituents mentioned.

Amongst the amine oxide compounds of the formula (1), in which the brightener radical A has the formula (3) or (4), particularly preferred compounds are those of the formula

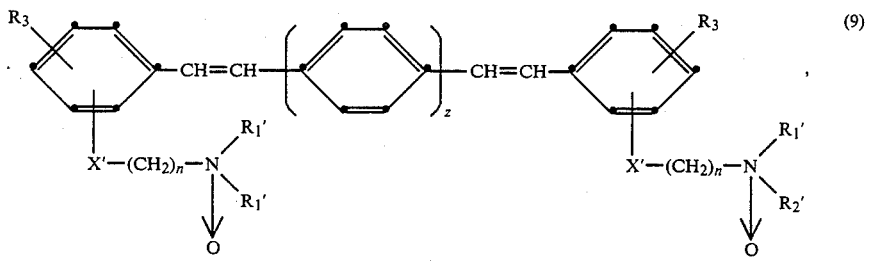

in which z is the integer 1 or 2 and n is an integer between 1 and 4, X', $R_1'$ and $R_2'$ are defined as under formula (2) and $R_3$ is halogen, alkyl having 1 to 4 carbon atoms, cycloalkyl having 5 or 6 carbon atoms, alkoxy having 1 to 4 carbon atoms, alkylsulfonyl having 1 to 4 carbon atoms, phenylsulfonyl, carbalkoxy having 2 to 5 carbon atoms, carbamoyl or sulfamoyl.

Amongst the compounds of the formula (9), those of the formula

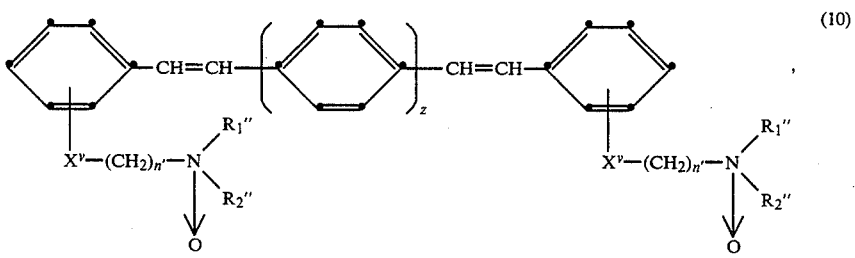

in which z is the integer 1 or 2, $X^v$ is an oxygen atom or a group of the formula —SO₂N(R')—, R' being hydrogen or alkyl which has 1 to 4 carbon atoms and is unsubstituted or substituted by hydroxyl, cyano or halogen, n' is an integer between 1 and 3 and $R_1''$ and $R_2''$ independently of one another are alkyl or hydroxyalkyl having 1 to 4 carbon atoms are preferred, and those of the formula

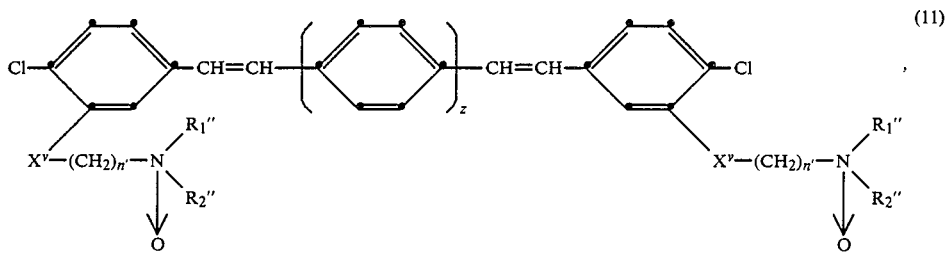

in which z is the integer 1 or 2, $X^y$ is an oxygen atom or a group of the formula $-SO_2N(R')$, R' being hydrogen or alkyl which has 1 to 4 carbon atoms and is unsubstituted or substituted by hydroxyl, cyano or halogen, n' is an integer between 1 and 3 and $R_1''$ and $R_2''$ independently of one another are alkyl or hydroxyalkyl having 1 to 4 carbon atoms, and those of the formula

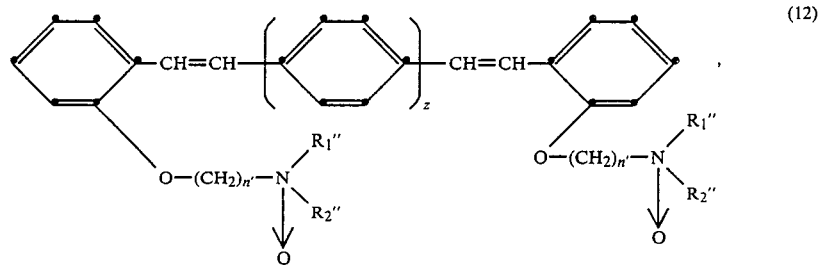

in which z, n', $R_1''$ and $R_2''$ are defined as under formula (10), are particularly preferred.

Amongst the amine oxide compounds of the formula (1), which contain a brightener radical A of the formula (8), those of the formula

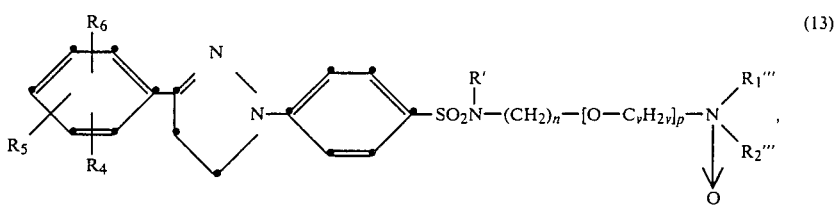

in which $R_4$ is hydrogen or halogen, $R_5$ and $R_6$ are each hydrogen, halogen, alkyl or alkoxy each having 1 to 4 carbon atoms, n and v are each an integer between 1 and 4, p is 0 or 1, R' is hydrogen or alkyl having 1 to 4 carbon atoms, which is unsubstituted or substituted by hyroxyl, cyano or halogen, $R_1'''$ and $R_2'''$ independently of one another are alkyl having 1 to 8 carbon atoms, which is unsubstituted or substituted by halogen, cyano, hydroxyl, alkoxy having 1 to 4 carbon atoms, phenyl, chlorophenyl, methoxyphenyl, methylphenyl or alkoxycarbonyl having 2 to 5 carbon atoms, or, if n is 2 or 3 and p is 0, R' and $R_1'''$ conjointly are an ethylene or methylene group, thereby forming a group of the formula

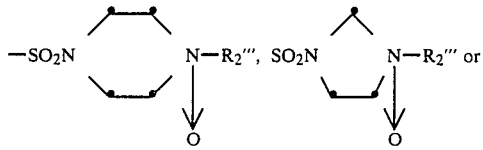

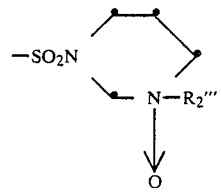

are preferred.

Amongst the last-mentioned compounds, those of the formula

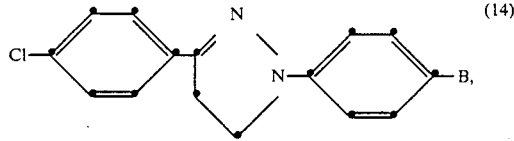

in which B is a group of the formula

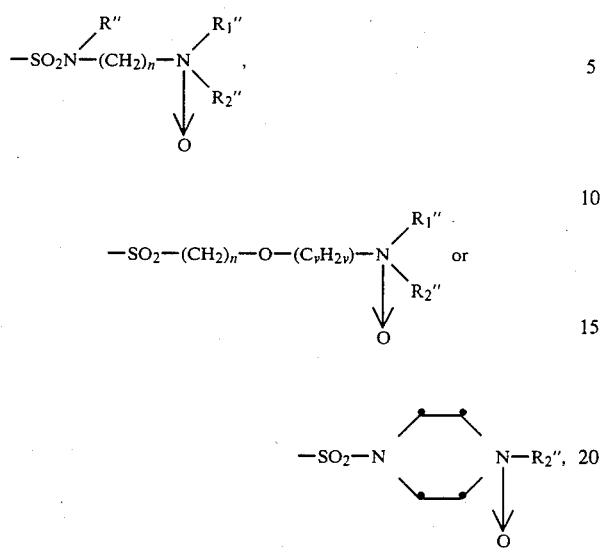

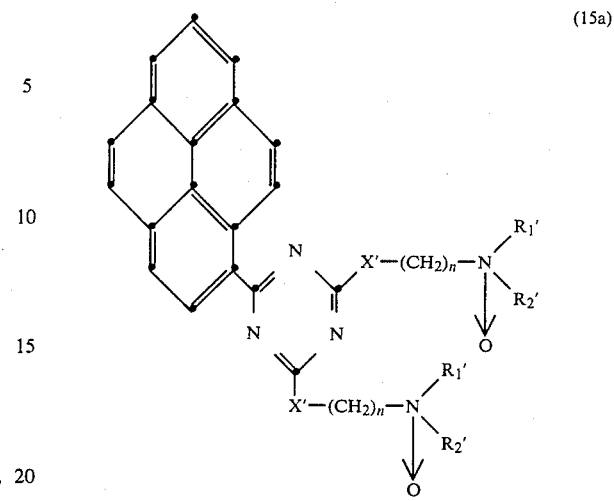

(15a)

in which n is an integer between 1 and 4 and X′, R$_1$′ and R$_2$′ are as defined in formula 2, X′ preferably being oxygen and R$_1$′ and R$_2$′ preferably being, independently of one another, alkyl or hydroxyalkyl having 1 to 4 carbon atoms, are particularly preferred.

in which R″ is hydrogen or alkyl, hydroxyalkyl or cyanoalkyl, each having 1 to 4 carbon atoms in the alkyl moiety, R$_1$″ and R$_2$″ are each alkyl or hydroxyalkyl having 1 to 4 carbon atoms and n and v are each an integer between 1 and 4, are particularly preferred.

Particularly advantageous compounds of the formula (1), in which A is a brightener radical of the formula (5), are those of the formula The amine oxide compounds according to the invention, of the formula (1), can be prepared by processes known per se.

Thus, compounds of the formula (1), in which X is a direct bond between A and Y or is an oxygen atom or a group of the formula —SO$_2$—O—, —SO$_2$—, —COO—, —CON(R)— or —SO$_2$N(R)—, can be prepared by oxidising a compound of the formula

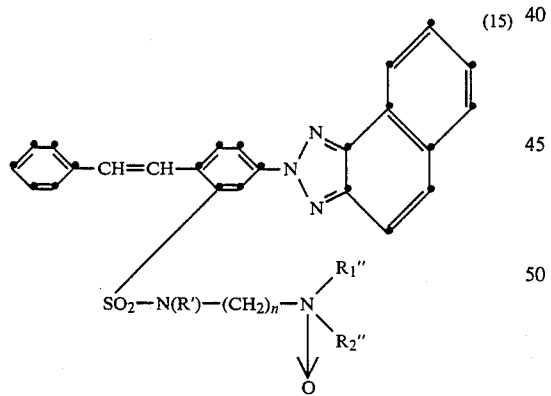

(15)

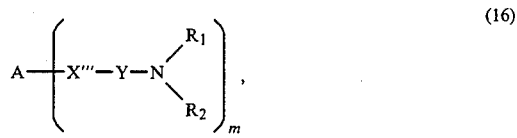

(16)

in which A, Y, R$_1$, R$_2$ and m are as defined under formula (1) and X‴ is a direct bond between A and Y or is an oxygen atom or sulfur atom or a group of the formula —SO—, —SO$_2$—O—, —SO$_2$—, —COO—, —CON(R)— or —SO$_2$N(R)—, in which R is also as defined under formula (1).

Compounds of the formula (16), in which X‴ is —S— or —SO— are thereby oxidised to compounds of the formula (1) in which X is —SO$_2$—.

in which R′ is hydrogen or alkyl, hydroxyalkyl, cyanoalkyl or halogenoalkyl, each having 1 to 4 carbon atoms in the alkyl moiety, R$_1$″ and R$_2$″ are each alkyl or hydroxyalkyl having 1 to 4 carbon atoms and n is an integer between 1 and 4.

Amongst the compounds of the formula (1), in which A is a brightener radical of the formula (8a), those of the formula The oxidation of the compounds of the formula (16) is preferably carried out by means of a per-compound. These can be inorganic and organic compounds which contain oxygen-oxygen bonds (—O—O—) in their molecule, for example hydrogen peroxide, peroxymonosulfuric acid (Caro's acid), ozone, performic acid, peracetic acid or unsubstituted or substituted (for example chlorine-substituted or methyl-substituted)perbenzoic acid. Compounds of particular importance in practice are hydrogen peroxide, performic acid and peracetic acid. A mixture of different per-compounds can also be used. Such mixtures can in particular be used if the per-compound is an organic compound produced in situ by oxidising an organic acid, for example formic acid or acetic acid, by means of excess hydrogen peroxide.

When hydrogen peroxide, performic acid or peracetic acid is used, it is preferred to employ dilute solutions of these per-compounds, for example a 30% strength hydrogen peroxide solution. The amount of oxidising agent to be employed varies within wide limits and naturally depends largely on the oxidising power of the per-compound employed and on the reactivity of the amine to be oxidised. Advantageously, an equivalent amount of per-compound is used; an excess of up to several times the equivalent amount can however also be used, especially in order to ensure a rapid reaction.

The oxidation of the starting materials of the formula (16) to the amine oxide compounds according to the invention, of the formula (1), is advantageously carried out in a solvent which is inert under the reaction conditions. Suitable solvents are apolar and dipolar, aprotic and protic solvents, for example cyclohexane, toluene, xylene, chlorobenzene, methylene chloride, 1,2-dichloroethane, chloroform, acetone, methyl ethyl ketone, dioxane, dimethylformamide, diethylformamide, N-methylpyrrolidone, ethanol, isopropanol, acetic anhydride and the like. The oxidation can also be carried out in water or in water-containing mixtures in the presence or absence of phase transfer catalysts.

The oxidation of the starting materials of the formula (16) to the amine oxide compounds according to the invention, of the formula (1), is preferably carried out in a water-miscible organic solvent in which the starting materials of the formula (16) are partially or completely soluble, for example in acetone, methyl ethyl ketone or dioxane. The amine oxide compounds according to the invention, of the formula (1), very often precipitate in a crystalline form during the oxidation and are isolated by filtration. The amine oxide compounds of the formula (1), which in this way are isolated in a virtually pure state, are preferably employed as fluorescent brighteners without prior purification.

The temperature during the oxidation can vary within wide limits depending on the chosen oxidising agent and on the solvent used, and can easily be determined by preliminary experiments. The oxidation of the starting materials of the formula (16) to give the amine oxide compounds according to the invention, of the formula (1), is accordingly advantageously carried out at temperatures of between $-10°$ C. and the boiling point of the solvent used; preferably, however, the oxidation is carried out at temperatures of between 20° and 50° C.

The oxidation of the starting materials of the formula (16) to give the amine oxide compounds according to the invention, of the formula (1), can in certain cases preferably be carried out in the presence of catalytic amounts of inorganic per-compounds of acid-forming elements of groups VA, VIA, VIB and VIII of the periodic table, as defined in U.S. Pat. No. 3,047,579.

A further process for the preparation of compounds according to the invention, namely of those compounds of the formula (1) in which R and $R_1$ conjointly cannot serve to complete a nitrogen-containing heterocyclic ring, comprises reacting one mol equivalent of a compound of the formula

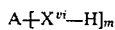  (17)

with m mol equivalents of a compound of the formula

  (18)

in which formulae A, m, Y, $R_1$ and $R_2$ are as defined under formula (1) (with the exception of the conjoint meaning of $R_1+R$), Hal is chlorine or bromine and $X^{vi}$ is an oxygen atom or sulfur atom or a group of the formula $-SO_2-$ or $-COO-$.

Compounds of the formula (1), in which X is a group of the formula $-SO_2-O-$ or $-COO-$, can also be prepared by reacting a compound of the formula

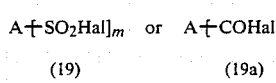

with m mol equivalents of a compound of the formula

  (20)

in which formulae (19), (19a) and (20) A, m, Y, $R_1$ and $R_2$ are as defined under formula (1) and Hal is chlorine or bromine.

The reaction of compounds of the formula (17) with compounds of the formula (18) or of compounds of the formula (19) or (19a) with compounds of the formula (20) is advantageously carried out in an inert organic solvent (see above) and in the presence of a weak or strong inorganic or organic base, in a manner known per se.

The starting compounds of the formula (16) are known, for example from U.S. Pat. No. 4,151,163, Belgian Patent Specification No. 722,233, British Patent Specification No. 1,186,650, German Offenlegungsschrift No. 2,921,641 and European Laid-Open Applications Nos. 19,702 or 19,078 or can be obtained analogously to the processes described there.

Starting compounds of the formula (16), in which $X'''$ is a direct bond between A and Y, are advantageously obtained by chloromethylating a brightener system A and then reacting the chloromethylated brightener with a corresponding secondary amine or with a tertiary amine containing a functional group in an alkyl group; cf. Swiss Patent Specification No. 439,293.

In general, the compounds of the formula (16) can also be obtained by the process described above for the preparation of compounds of the formula (1), namely by reacting either one mol equivalent of a compound of the formula

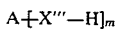  (21)

with m mol equivalents of a compound of the formula

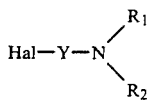

(22)

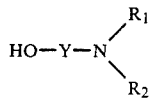

(23)

in which the general symbols have the meaning given above. The reaction conditions are analogous to those for the reaction of compounds of the formula (17) with compounds of the formula (18) or of compounds of the formula (19) or (19a) with compounds of the formula (20).

The amines of the formulae (22) and (23) are known from the literature and in the majority of cases are available commercially.

The amine oxides of the formula (18) and (20) can be obtained easily by oxidising amines of the formulae (22) and (23) by means of per-compounds. Such oxidations are described in detail in the literature (Houben-Weyl, "Methoden der organischen Chemie" ("Methods of Organic Chemistry"), fourth edition, Volume XI/2, pages 191–200 (1958); J. Org. Chem. 11, 586–591 (1946); British Patent Specification No. 761,001).

The compounds of the formulae (17), (19), (19a) and (21) are known from the patent literature or can be prepared by methods which are known per se. For example, those of the pyrazoline category can be prepared as described in Swiss Patent Specifications Nos. 492,069, 386,430 and 475,255, those of the stilbene category as described in Swiss Patent Specification No. 467,819, U.S. Defensive Publication No. 778,781, Japanese Patent Specification No. 6,982/69 and Swiss Patent Specification No. 603,513, those of the 1,4-bis-styrylbenzene category as described in German Offenlegungsschrift No. 2,039,993 and those of the 1,4-bis-styrylbiphenyl category as described in Swiss Patent Specification No. 513,785.

The processes, mentioned above, for the preparation of the compounds according to the invention, of the formula (1), start from an already formed brightener structure which, if it does not yet contain a tertiary amino group, is either first linked to m radicals which carry tertiary amino groups and is then oxidised by means of per-compounds to give the compounds of the formula (1), or is linked to m radicals which carry amine oxide groups, so as to give the compounds of the formula (1) direct.

In some cases it can however be more advantageous to prepare the compounds according to the invention, of the formula (1), by synthesis of the actual brightener structure from units which already contain amine oxide groups. Thus, for example, the compounds according to the invention, of the formula

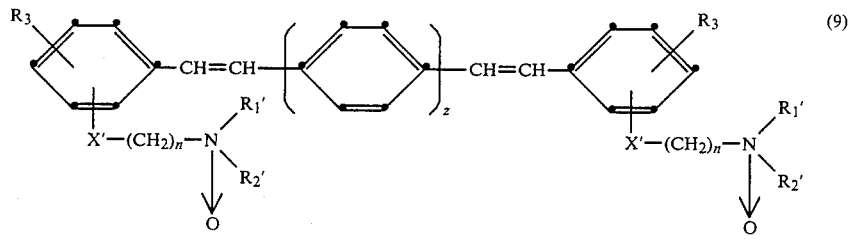

(9)

can be prepared by condensing 2 mol equivalents of an amine oxide of the formula

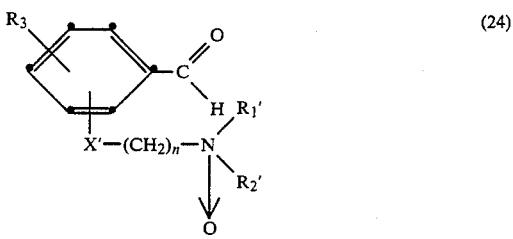

(24)

with one mol equivalent of a compound of the formula

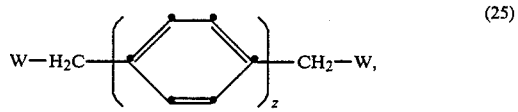

(25)

in which formulae $R_1'$, $R_2'$, $R_3$, $X'$, z and n are as defined in formula (9) and W is a radical of the formula —COOV, in which V is alkyl, or W is

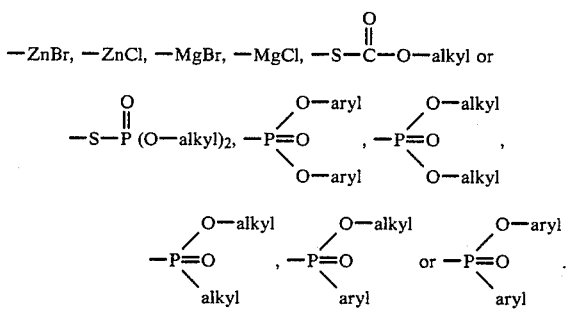

The amine oxides of the formula (24) can easily be prepared by oxidising the amines (known from the literature) of the formula

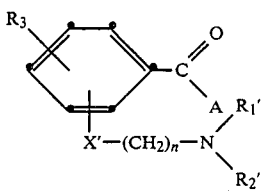

(26)

with per-compounds. The compounds of the formula (25) are known from the literature.

The novel compounds of the formula (1), defined above, exhibit a more or less pronounced fluorescence in the dissolved or finely divided state. They are therefore used for the fluorescent brightening of a great variety of synthetic, semi-synthetic or natural organic materials.

Without intending to imply any limitation through the list which follows, examples of suitable organic materials are the following groups, to the extent that fluorescent brightening thereof is relevant:

I. Synthetic organic materials of high molecular weight:

(a) Polymerisation products based on organic compounds containing at least one polymerisable carbon-carbon double bond, that is to say their homopolymers or copolymers as well as their after-treatment products, for example crosslinking, grafting or degradation products, polymer blends, or products obtained by modification of reactive groups, for example polymers based on $\alpha,\beta$-unsaturated carboxylic acids or derivatives of such carboxylic acids, especially on acrylic compounds, (for example acrylates, acrylic acid, acrylonitrile, acrylamides or their derivatives and their methacrylic analogues), on olefin hydrocarbons (for example ethylene, propylene, styrenes or dienes and also ABS polymers), and polymers based on vinyl and vinylidene compounds (for example vinyl chloride, vinyl alcohol and vinylidene chloride);

(b) Polymerisation products which can be obtained by ring opening, for example polyamides of the polycaprolactam type, and also polymers which are obtained both by polyaddition and by polycondensation, for example polyethers or polyacetals;

(c) Polycondensation products or precondensates based on bifunctional or polyfunctional compounds with condensable groups, their homocondensation and co-condensation products, and after-treatment products thereof, for example polyesters, in particular saturated polyesters (for example polyesters of ethylene glycol terephthalic acid) or unsaturated polyesters (for example maleic acid-dialcohol polycondensates and their crosslinking products with copolymerisable vinyl monomers), unbranched and branched polyesters (also including those based on polyhydric alcohols, for example alkyd resins), polyamides (for example polyhexamethylenediamine adipate), maleic resins, melamine resins, the precondensates and analogues thereof, polycarbonates and silicones;

(d) Polyaddition products, such as polyurethanes (crosslinked and uncrosslinked) and epoxide resins.

II. Semi-synthetic organic materials, for example, cellulose esters of varying degrees of esterification (so-called 2½-acetate or triacetate) or cellulose ethers, regenerated cellulose (viscose or cuprammonium cellulose), or their after-treatment products, and casein plastics.

III. Natural organic materials of animal or vegetable origin, for example based on cellulose or proteins, such as cotton, wool, linen, silk, varnish gums, starch and casein.

The organic materials to be optically brightened can be in the most diverse states of processing (raw materials, semi-finished goods or finished goods). On the other hand, they can be in the form of structures of the most diverse shapes, for example predominantly three-dimensional structures, such as sheets, profiles, injection mouldings, various machined articles, chips, granules or foams, and also predominantly two-dimensional structures, such as films, foils, lacquers, coatings and impregnations or predominantly one-dimensional bodies, such as filaments, fibres, flocks and wires. The said materials can, on the other hand, also be in an unshaped state, in the most diverse homogeneous or inhomogeneous forms of division, as for example in the form of powders, solutions, emulsions, dispersions, latices, pastes or waxes.

Fibrous materials can be, for example, in the form of endless filaments (stretched or unstretched), staple fibres, flocks, hanks, textile filaments, yarns, threads, non-wovens, felts, waddings, flocked structures or woven textile or bonded textile fabrics, knitted fabrics and papers, cardboards or paper pulps.

The compounds to be used according to the invention are of importance, inter alia, for the treatment of organic textile materials, especially woven textile fabrics. If fibres, which can be in the form of staple fibres or endless filaments or in the form of hanks, woven fabrics, knitted fabrics, fleeces, flocked substrates or bonded fabrics, are to be subjected to fluorescent brightening according to the invention, this is advantageously effected in an aqueous medium, wherein the compounds in question are present in a finely divided form (suspensions, so-called microdispersions, or, where appropriate, solutions). If desired, dispersing agents, stabilisers, wetting agents and further assistants can be added during the treatment.

Depending on the type of brightener compound used, it can be advantageous to carry out the treatment in a neutral or alkaline or acid bath. The treatment is usually carried out at temperatures between about 20° and 140° C., for example at the boiling point of the bath or near it (about 90° C.). Solutions or emulsions in organic solvents can also be used for the finishing, according to the invention, of textile substrates, as is practised in the dyeing industry in so-called solvent dyeing (pad-thermofixation, or exhaust dyeing processes in dyeing machines).

The novel fluorescent brighteners of the invention can also be used to brighten paper pulps, inter alia also in the presence of, e.g., cationic retention agents and other additives.

The novel fluorescent brighteners of the present invention can further be added to, or incorporated in, the materials before or during their shaping. Thus they can for example be added to the compression moulding composition or injection moulding composition during the manufacture of films, sheets (for example incorporated in polyvinyl chloride in a roll mill at elevated temperature) or mouldings.

If the shaping of man-made fully synthetic or semi-synthetic organic materials is effected by spinning processes or from spinning compositions, the fluorescent brighteners can be applied by the following processes: addition to the starting substances (for example monomers) or intermediates (for example precondensates or prepolymers), that is to say before or during the polymerisation, polycondensation or polyaddition; sprinkling in powder form on polymer chips or granules for spinning compositions; bath dyeing of polymer chips or granules for spinning compositions; metered addition to spinning melts or spinning solutions; application to the spun tow before stretching.

The novel fluorescent brighteners of the present invention can, for example, also be employed in the following use forms:

(a) in mixtures with dyestuffs (shading) or pigments (coloured pigments or especially, for example, white pigments), or as an additive to dye baths, printing pastes, discharge pastes or reserve pastes, or for the aftertreatment of dyeings, prints or discharge prints;

(b) in mixtures with carriers, wetting agents, plasticers, swelling agents, antioxidants, light stabilisers, heat stabilisers and chemical bleaching agents (chlorite bleach or bleaching bath additives);

(c) in admixture with crosslinking agents or finishing agents (for example starch or synthetic finishes), and in combination with a wide variety of textile finishing processes, especially resin finishes (for example crease-proof finishes such as wash-and-water, permanent-press or non-iron), as well as flameproof finishes, soft-handle finishes, anti-soiling finishes or antistatic finishes, or antimicrobial finishes;

(d) incorporation of the fluorescent brighteners into polymeric carriers (polmerisation, polycondensation or polyaddition products), in dissolved or dispersed form, for use, for example, in coating agents, impregnating agents or binders (solutions, dispersions and emulsions) for textiles, non-wovens, papers and leather;

(e) as additives to a wide variety of industrial products in order to render these more marketable (for example improving the appearance of soaps, detergents or pigments);

(f) in combination with other fluorescent brightening substances;

(g) in spinning bath preparations, that is to say as additives to spinning baths which are used for improving the slip for the further processing of synthetic fibres, or from a special bath before the stretching of the fibre, for example as an after-treatment of wet-spun polyacrylic fibres in the gel state;

(h) as scintillators for various purposes of a photographic nature, for example for electrophotographic reproduction or supersensitising;

(i) depending on the substitution, as laser dyes.

If the brightening process is combined with textile treatment or finishing methods, the combined treatment can in many cases advantageously be carried out with the aid of appropriate stable preparations which contain the fluorescent brightener compounds in such a concentration that the desired brightening effect is achieved.

In certain cases, the brighteners are made fully effective by an after-treatment. This can be, for example, a chemical treatment (for example acid treatment), a thermal treatment, or a combined chemical/thermal treatment. Thus, for example, the appropriate procedure to follow in fluorescent brightening of a number of fibre substrates, for example polyester fibres, with the brighteners of the present invention, is to impregnate these fibres with the aqueous dispersions (or where appropriate also solutions) of the brighteners at temperatures below 75° C., for example at room temperature, and to subject them to a dry heat treatment at temperatures above 100° C., it being generally advisable additionally to dry the fibrous material beforehand at a moderately elevated temperature, for example at not less than 60° C. to about 130° C. The heat treatment in the dry state is then advantageously carried out at temperatures between 120° and 225° C., for example by heating in a drying chamber, by ironing within the specified temperature range or by treatment with dry, superheated steam. The drying and dry heat treatment can also be carried out in immediate succession or combined in a single operation.

The amount of novel fluorescent brightener to be used according to the invention, based on the weight of the material to be brightened, can vary within wide limits. A marked and lasting effect can be obtained even with very insignificant amounts, in certain cases, for example, 0.0001 percent by weight. However, it is also possible to use amounts of up to about 0.8 percent by weight and, where necessary, up to about 2 percent by weight. For most practical purposes, it is preferable to use amounts of between 0.0005 and 0.5 percent by weight.

For various reasons it is often advantageous not to use the fluorescent brighteners by themselves, i.e. pure, but in admixture with a wide variety of assistants and extenders, for example anhydrous sodium sulfate, sodium sulfate decahydrate, sodium chloride, sodium carbonate, alkali metal phosphates, such as sodium or potassium orthophosphate, sodium or potassium pyrophosphate and sodium or potassium tripolyphosphates or alkali metal silicates.

The novel fluorescent brighteners are also particularly suitable for use as addtives to wash liquors or heavy duty and domestic detergents and laundry aftertreatment agents, to which they can be added in various ways. They are appropriately added to wash liquors in the form of their solutions in water or organic solvents, or, in a finely divided form, as aqueous dispersions. They are advantageously added to domestic or heavy duty detergents in any stage of the manufacturing process of the detergents, for example to the slurry before the washing powder is atomised, or during the preparation of liquid detergent combinations. They can be added either in the form of a solution or dispersion in water or other solvents or, without assistants, as a dry brightening powder. For example, the brighteners can be mixed, kneaded or ground with the active detergents and, in this form, admixed to the finished powder. However, they can also be sprayed in a dissolved or pre-dispersed form onto the finished detergent.

Suitable detergents are the known mixtures of active detergents, for example soap in the form of chips and powders, synthetics, soluble salts of sulfonic acid hemiesters of higher fatty alcohols, arylsulfonic acids with higher and/or multiple alkyl substituents, sulfocarboxylic acid esters of medium to higher alcohols, fatty acid acylaminoalkyl- or acylaminoaryl-glycerol sulfonates, phosphoric acid esters of fatty alcohols and the like. Suitable builders which can be used are, for example, alkali metal polyphosphates and polymetaphosphates, alkali metal pyrophosphates, alkali metal salts of carboxymethylcellulose and other soil redeposition inhibitors, and also alkali metal silicates, alkali metal carbonates, alkali metal borates, alkali metal perborates, nitrilotriacetic acid, ethylenediaminetetraacetic acid, and foam stabilisers, such as alkanolamides of higher fatty acids. The detergents can further contain, for example: antistatic agents, fat-restorative skin protectives, such as lanolin, enzymes, antimicrobial agents, perfumes and colorants.

The compounds according to the invention are added in amounts of 0.005 to 1% or more, based on the weight of the finished detergent in liquid or powder form. Wash liquors which contain the indicated amounts of the claimed fluorescent brighteners impart a brilliant appearance in daylight when used to wash textiles made from cellulose fibres, polyamide fibres, resin-finished cellulose fibres, polyester fibres, wool and the like.

The washing treatment is carried out, for example, as follows:

The stated textiles are treated for 1 to 30 minutes at 20° to 100° C. in a wash liquor which contains 1 to 10 g/kg of a built-up composite detergent and 0.05 to 1%, based on the weight of the detergent, of the claimed brightener. The liquor ratio can be 1:3 to 1:50. After they have been washed, the textiles are rinsed and dried in the usual manner. The wash liquor can contain 0.2 g/l of active chlorine (for example as hypochlorite) or 0.1 to 2 g/l of sodium perborate as a bleaching additive.

The compounds according to the invention can also be employed in an after-rinse bath, such as is conventionally used for merely imparting a soft handle, antistatic properties, anti-soil effect, scents and the like. In particular, they are suitable for use in laundry after-treatment agents which contain cationic softeners.

The novel fluorescent brighteners are also very suitable for use as brighteners for concentrated liquid washing agents which contain non-ionic surfactants and cationic softeners or surfactants.

The present invention accordingly also relates to a washing agent which is preferably in liquid form and which contains non-ionic surfactants and cationic textile softeners in addition to the novel amine oxide compounds and the conventional additives.

Suitable non-ionic surfactants are those usually encountered in commerce, for example the water-soluble products which result from adduct formation of an alkylene oxide, or of an equivalent compound, with a reactive hydrogen atom of a hydrophobic compound. The hydrophobic organic products can be heterocyclic compounds and, in particular, aliphatics or aromatics. Preferred compounds are higher aliphatic alcohols and alkylphenols, but other compounds, for example carboxylic acids, carboxamides, mercaptans, sulfamides and the like, can also be used. Preferred non-ionic compounds are the adducts of ethylene oxide with higher aliphatic alcohols, having 6 to 50, or more, carbon atoms. The amount of ethylene oxide can vary within wide limits but in general at least 5 mols of ethylene oxide are required per mol of hydrophobic substance. It is also possible entirely or partially to replace the ethylene oxide by other lower alkylene oxides, for example propylene oxide and butylene oxide. Other possible non-ionic cuompounds are:

(a) Polyoxyalkylene esters of organic acids, such as higher fatty acids, resin acids, tallow oil acids and acids of petroleum oxidation products, the esters as a rule having 10 to 22 carbon atoms in the acid moiety and containing about 12 to about 30 mols of ethylene oxide or of its equivalent.

(b) Alkylene oxide adducts of higher fatty acid amides, the fatty acid moiety as a rule having 8 to 22 carbon atoms and being condensed with 10 to 50 mols of ethylene oxide. The corresponding carboxamides and sulfamides can also be used as being substantially equivalent.

In the preparation of liquid concentrated detergents, the non-ionic surfactants used are preferably oxyalkylated higher aliphatic alcohols, the fatty alcohols having at least 6 and preferably at least 8 carbon atoms. Preferred alcohols are lauryl alcohol, myristyl alcohol, cetyl alcohol, stearyl alcohol and oleyl alcohol, which are condensed with not less than 6 mols of ethylene oxide. A typical non-ionic product is the adduct of an aliphatic alcohol having 12–13 carbon atoms with about 6.5 mols of ethylene oxide. The corresponding alkylmercaptans can, after condensation with ethylene oxide, also be used as non-ionic surfactants.

The oxyalkylated higher aliphatic alcohols are particularly suitable for domestic detergents, since they are easily biologically degradable and have good compatibility with cationic surfactants and textile softeners and with the other additives.

Suitable cationic textile softeners are, inter alia, particularly quaternary derivatives of ammonia and/or of imidazoline, having 2 long-chain aliphatic saturated or unsaturated radicals.

Examples of these textile softeners are:

(1) Quaternary ammonium salts of the formula

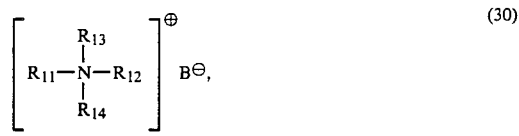

(30)

in which $R_{11}$ is hydrogen or an aliphatic group having 1 to 22 carbon atoms, $R_{12}$ is an aliphatic group having 10 to 22 carbon atoms, $R_{13}$ and $R_{14}$ independently of one another are alkyl having 1 to 4 carbon atoms and $B^\ominus$ is an anion. The anion $B^\ominus$ can be any desired anion, as a rule introduced through the quaternisation reaction. Preferably, it is a halogen ion (including $I^\ominus$), an alkylsulfate ion, an alkanesulfonate ion or an arylsulfonate ion, for example the phenyl-sulfate ion, p-tolyl-sulfate ion and p-chlorophenylsulfonate ion. However, it can also be a sulfate, sulfite, carbonate, phosphate, nitrate, acetate, oxalate, citrate or lactate ion or some other anion of an organic carboxylic acid.

Examples of quaternary ammonium softeners are tallyltrimethylammonium chloride, ditallyldimethylammonium chloride, ditallyldimethylammonium sulfate, dihexadecyldimethylammonium chloride, dioctadecyldimethylammonium chloride, dieicosyldimethylammonium chloride, didocosyldimethylammonium chloride, dihexadecyldiethylammonium chloride, dihexadecyldimethylammonium acetate, ditallyldipropylammonium phosphate, ditallyldimethylammonium nitrate and dicocoyldimethylammonium chloride.

(2) Quaternary imidazolinium salts of the formula

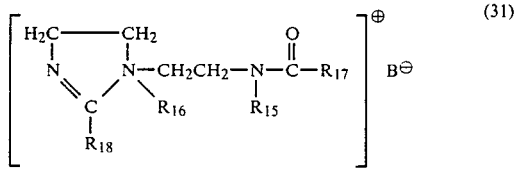

(31)

in which $R_{15}$ is hydrogen or alkyl having 1 to 4 carbon atoms, $R_{16}$ is alkyl having 1 to 4 carbon atoms, $R_{17}$ is alkyl having 1 to 22 carbon atoms, $R_{18}$ is hydrogen or alkyl having 1 to 22, preferably 15–22, carbon atoms and $B^{\ominus}$ is an anion.

The anion $B^{\ominus}$ is as defined under formula (30).

However, preferred compounds of the formula (31) are those in which $R_{17}$ and $R_{18}$ are each alkyl having 12 to 22 carbon atoms.

Examples of preferred imidazolinium compounds of the formula (31) are 1-methyl-1-stearoylamidoethyl-2-heptadecyl-imidazolinium methosulfate, 1-methyl-1-palmitoylamidoethyl-2-octadecyl-imidazolinium chloride and 2-tallyl-1-methyl-1-talloylamidoethyl-imidazolinium methosulfate.

Further examples of suitable textile softeners are 1-methyl-1-oleylamidoethyl-2-oleyl-imidazolinium. $X^{\ominus}$, 1-methyl-1-talloylamidoethyl-2-tallylimidazolinium. $X^{\ominus}$, ditallyl-dimethylammonium. $X^{\ominus}$ or a compound of the formula

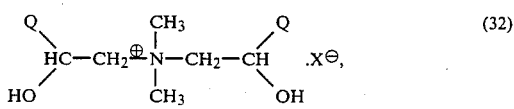

(32)

in which Q is $C_{14}$–$C_{16}$-alkyl and $X^{\ominus}$ is a chloride, bromide, methylsulfate, ethylsulfate, methanesulfonate, ethanesulfonate or toluenesulfonate anion.

Amongst the cationic textile softeners, quaternary imidazolinium compounds such as 1-methyl-1-oleylamidoethyl-2-oleyl-imidazolinium methosulfate and 1-methyl-1-talloylamidoethyl-2-tallyl-imidazolinium methosulfate are particularly suitable.

The said quaternary textile softeners and especially the two last-mentioned compounds impart a soft and fluffy handle, and good ease of remoistening, to the fabric. These textile softeners are substantive towards the fabric and contribute to reducing electrostatic charges and reducing the tendency to crease, so that the fabric can be ironed more easily and is pleasanter to wear.

The liquid medium for the detergents according to the invention is aqueous and can consist of water alone or of water and additional solvents for certain adjuvants. The additional solvents can account for up to 20%, preferably up to 15%, of the total solvent medium. Suitable additional solvents include lower alkanols, lower diols or polyols, for example ethanol, isopropanol, ethylene glycol, propylene glycol and glycerol. Etherified polyols, such as diethylene glycol, ethylene glycol dimethyl ether and ethylene glycol monoethyl ether can also be used as additional solvents.

The liquid detergent according to the invention can contain various selected compatible additives, such as soil-suspending agents or graying inhibitors, for example polyvinyl alcohol and hydroxypropylmethylcellulose; foam inhibitors; preservatives, for example sodium benzoate; UV absorbers and perfumes. Of course, these are selected so as to be compatible with the main components of the detergent.

The non-ionic surfactants are employed in amounts of 25 to 70% by weight, preferably about 60% by weight.

The concentration of the textile softener is 5 to 30% by weight, preferably about 21% by weight. The aqueous solvent, preferably water, which can additionally contain monohydric, dihydric and polyhydric alcohols and similar solvents, is present in an amount of 5 to 60% by weight. The finished liquid detergent contains the compounds according to the invention in amounts of 0.005 to 3% by weight. The content of other auxiliaries is preferably less than 5% by weight of the detergent, since the use of larger quantities can affect the properties of liquid detergents. Though the preferred detergent preparation according to the invention is a stable, clear liquid, it is possible to add a compatible clouding agent thereto, in order to create an opaque appearance.

The detergent according to the invention can be used in soft or moderately hard water, at elevated temperatures. At lower temperatures, the detergent can also be used for washing textiles in very hard water. The water hardness can accordingly vary between 0 and 300 ppm, calculated as calcium carbonate, and the washing temperature can be 4° to 60° C.

The detergent according to the invention dissolves very easily in cold or warm washing water, cleans thoroughly, eliminates static charge and gives the laundry a soft handle, without making it hydrophobic. The preferred detergent is in the form of a clear, stable liquid, which retains its activity and uniformity for a lengthy period of time. To prepare a clear liquid detergent, the concentration of the active substances must lie within certain limits. Thus, for example, the concentration of the textile softener should not be much higher than 30% if a clear liquid detergent is to be obtained.

The compounds according to the invention are added in amounts of 0.005 to 1% or more, relative to the weight of the liquid or pulverulent, finished detergent or textile treatment agent. Washing/treating liquors, which contain the stated amounts of the claimed brighteners, when used to wash textiles consisting of cellulose fibres, polyamide fibres, resin-finished cellulose fibres, polyester fibres, wool and the like, give textiles having a brilliant appearance in daylight.

The washing treatment is carried out by, for example, the following method:

The textiles mentioned are treated for 1 to 30 minutes, at 20° to 100° C., in a washing liquor which contains 0.1 to 10 g/kg of the particular detergent and 0.01 to 1%, relative to the weight of detergent, of the claimed brightener. The liquor ratio can be from 3:1 to 50:1. After washing, the textile is rinsed and dried in the usual manner.

In the examples, parts and percentages are by weight, unless stated otherwise. Melting points and boiling points are uncorrected, unless stated otherwise.

EXAMPLE 1

20.6 g of the compound of the formula

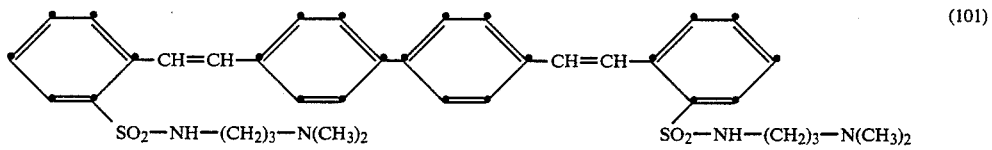

(101)

are dissolved in 500 ml of hot methyl ethyl ketone and 70 g of 30% hydrogen peroxide are added slowly at 40° C. The reaction mixture is then stirred for 60 hours at room temperature, in the course of which the reaction product precipitates in a crystalline form. It is filtered off, washed with 50 ml of methyl ethyl ketone and dried to constant weight in vacuo at 70° C. 20 g (about 93% of theory) of the compound of the formula

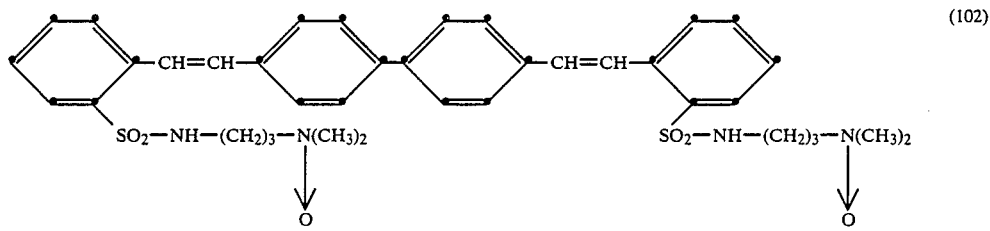
(102)

are obtained in the form of a pale yellow crystalline powder, which melts, with decomposition, at 192°-194° C. After one recrystallisation from alcohol/water, 18 g of the compound (102) are obtained in the form of pale yellow flakes of melting point 193°-195° C. (with decomposition). Starting from the corresponding amines, the amine oxide compounds of the formula

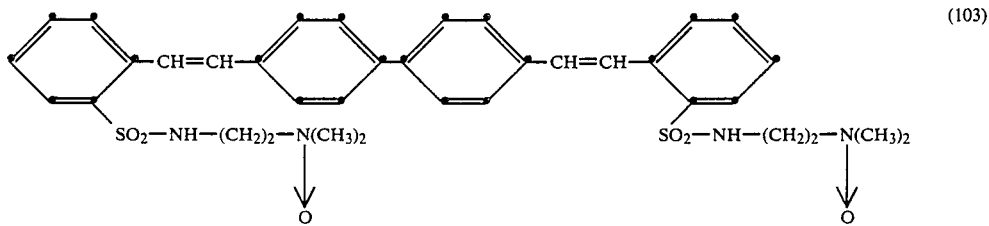
(103)

and of the formula

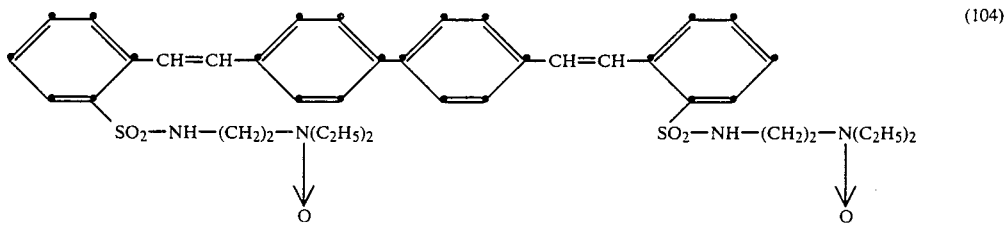
(104)

are obtained analogously, compound (103) being in the form of small yellow needles (from ethanol/water), which melt, with decomposition, at 182°-186° C., and compound (104) being in the form of pale yellow flakes which melt, with decomposition, at 164°-167° C.

The preparation of the starting compound of the formula (101) is described in Example 8 of British Patent Specification No. 1,247,934. Homologous compounds are prepared analogously.

EXAMPLE 2

28 g of the compound of the formula

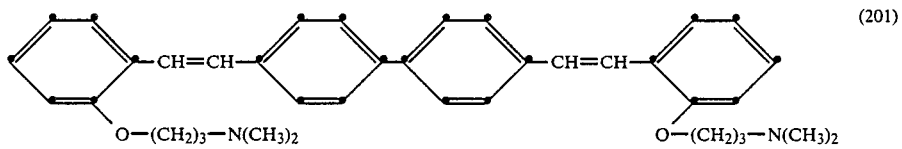
(201)

are dissolved in 500 ml of hot methyl ethyl ketone and 113 g of 30% hydrogen peroxide are added in the course of 10 minutes, at 50° C. The reaction mixture is then stirred for 48 hours at room temperature, in the course of which the reaction product precipitates in a crystalline form.

The product is filtered off, washed with 50 ml of methyl ethyl ketone and dried to constant weight in vacuo at 70° C.

28 g (about 95% of theory) of the compound of the formula

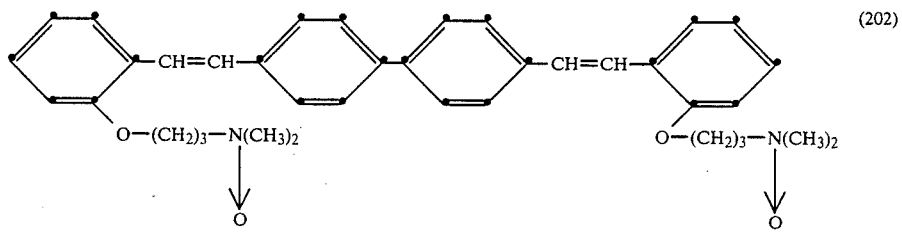

are obtained in the form of a yellow crystalline powder, melting at 170°–172° C.

After one recrystallisation from alcohol, 20.5 g of the compound of the formula (202) are obtained as pale yellow small needles of melting point 172°–173° C.

Starting from the corresponding amines, the amine oxide compounds of the formula

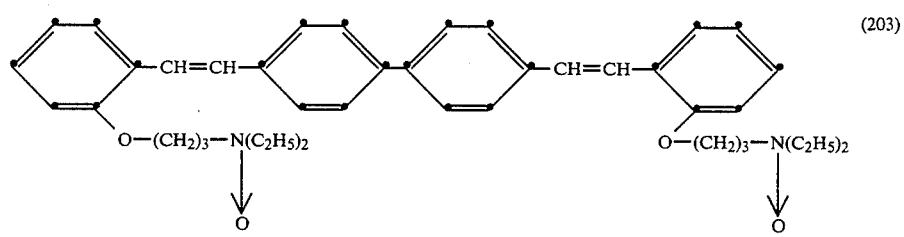

and of the formula

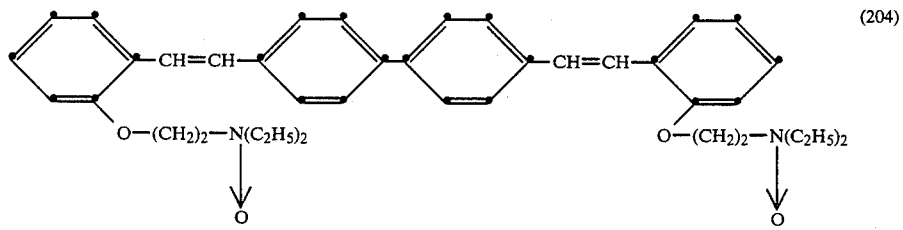

are obtained analogously, the compound (203) being in the form of yellow small needles which melt, with decomposition, at 143°–145° C., and the compound (204) being in the form of pale yellow flakes (from alcohol), which melt at 160°–162° C.

The preparation of the starting compound of the formula (201) is described in European Laid-Open Application 19,702. Homologous compounds are prepared analogously.

EXAMPLE 3

18.8 g of the compound of the formula are dissolved in 300 ml of methyl ethyl ketone and 45 g of 30% hydrogen peroxide are added in the course of 10 minutes, at room temperature. The reaction mixture is then stirred for a further 48 hours at room temperature, in the course of which the reaction product remains in solution. 2 g of palladium on charcoal (5% Pd) are then added to the clear solution obtained, with cooling, and stirring is continued overnight at room temperature, during which the excess hydrogen peroxide decomposes, with evolution of oxygen.

The palladium on charcoal is removed from the reaction mixture by filtration, and the clear reaction solution obtained is treated with 500 ml of water and freed from methyl ethyl ketone on a rotary evaporator, in vacuo.

A sample of the aqueous reaction solution is titrated with sodium thiosulfate to determine hydrogen peroxide; none is found to have remained. The aqueous reaction solution is then concentrated to dryness on a rotary evaporator in vacuo, and the reaction product is recrystallised from alcohol, using 5 g of active charcoal for decolorising. 15 g (about 68% of theory) of the compound of the formula

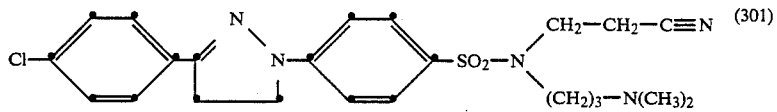

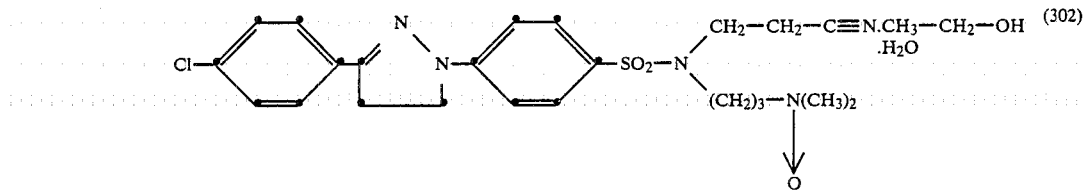

are obtained in the form of yellow small needles which melt, with decomposition, at 128°–133° C. After recrystallisation from ethyl acetate/methanol, 10.5 g of the compound of the formula (302) are obtained in the form of yellow small needles of melting point 136°–138° C. (with decomposition).

The preparation of the starting compound of the formula (301) is described in British Patent Specification No. 2,000,507.

EXAMPLE 4

21 g of the compound of the formula

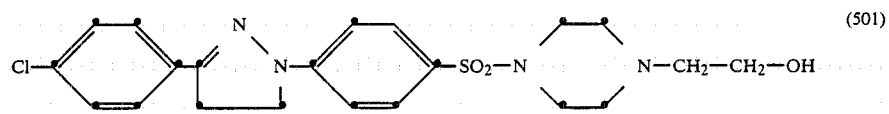

are dissolved in 300 ml of chloroform and a solution of 10 g of 85% m-chloroperbenzoic acid in 100 ml of chloroform is added in the course of 15 minutes at room temperature. The reaction mixture is then stirred further, first for 24 hours at room temperature and then for 3 hours under reflux. The clear reaction solution obtained is concentrated to dryness on a rotary evaporator in vacuo and the reaction product is recrystallised from alcohol. 26 g (about 88% of theory) of the compound of the formula

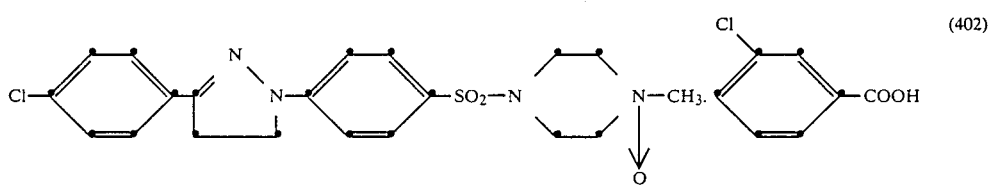

are obtained in the form of yellow small needles which melt, with decomposition, at 161° to 167° C. After two recrystallisations from alcohol, 21 g of the compound of the formula (402) are obtained in the form of yellow small needles of melting point 165°–166° C. (with decomposition).

The preparation of the starting compound of the formula (401) is described in Example 4 of British Patent Specification No. 1,186,650.

EXAMPLE 5

18 g of the compound of the formula (501)

Cl—⟨ring⟩—N=N—⟨ring⟩—SO$_2$—N⟨ring⟩N—CH$_2$—CH$_2$—OH are dissolved in 400 ml of chloroform and a solution of 8 g of 85% m-chloroperbenzoic acid in 80 ml of chloroform is added in the course of 15 minutes at room temperature. The reaction mixture is then stirred further, first for 24 hours at room temperature and then for 3 hours under reflux. The clear reaction solution obtained is concentrated to dryness on a rotary evaporator in vacuo and the reaction product is recrystallised from alcohol. 26 g (about 84% of theory) of the compound of the formula

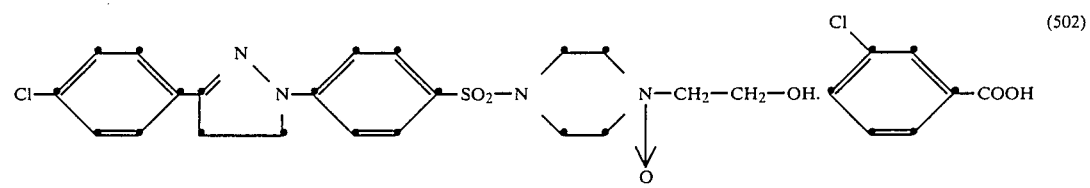

are obtained in the form of yellow needles which melt, with decomposition, at 148° to 150° C. After one recrystallisation from alcohol, 22 g of the compound of the formula (502) are obtained in the form of yellow needles of melting point 152°–154° C. (with decomposition).

If this compound is dissolved in hot alcohol and the solution is treated with active charcoal, 14 g of the free base, of the formula

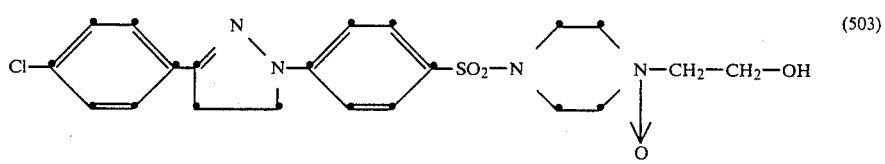
(503)

are obtained in the form of yellow small needles, which melt, with decomposition, at 196° to 199° C.

The preparation of the starting compound of the formula (501) is described in Example 1 of British Patent Specification No. 1,186,650.

EXAMPLE 6

20 g of the compound of the formula

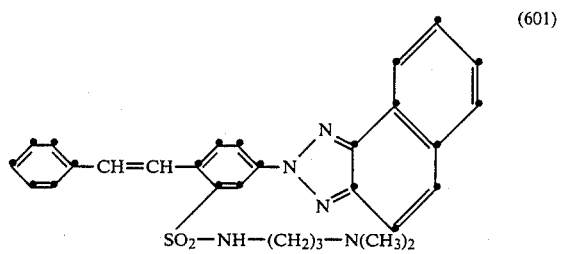
(601)

are dissolved in 400 ml of methyl ethyl ketone and 45 g of 30% hydrogen peroxide are added slowly at room temperature. The reaction mixture is then stirred for a further 48 hours at room temperature, in the course of which the reaction product precipitates in a crystalline form. The product is filtered off, washed with 50 ml of methyl ethyl ketone and dried to constant weight in vacuo at 70° C.

12 g (about 56% of theory) of the compound of the formula

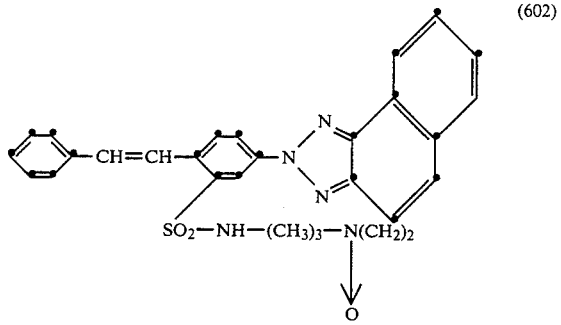
(602)

are obtained in the form of a yellow crystalline powder, which melts, with decomposition, at 157° to 160° C. After one recrystallisation from alcohol, 10 g of the compound of the formula (602) are obtained as pale yellow flakes of melting point 165°-170° C. (with decomposition).

The preparation of the starting compound of the formula (601) is described in Example 5 of British Patent Specification No. 917,242.

EXAMPLE 7

22.5 g of the compound of the formula

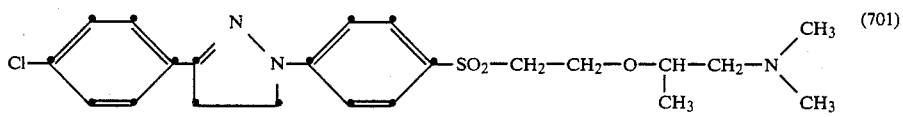
(701)

are dissolved in 250 ml of methyl ethyl ketone and 57 g of 30% hydrogen peroxide are added in the course of 10 minutes, at room temperature. The reaction mixture is then stirred for 20 hours at room temperature and 6 hours at 40° C., in the course of which the reaction product remains in solution.

The clear reaction solution obtained is worked up as described in Example 3, and after concentrating the aqueous reaction solution to dryness on a rotary evaporator in vacuo, the reaction product is recrystallised from isopropanol, using 5 g of active charcoal for decolorising.

17 g (about 73% of theory) of the compound of the formula

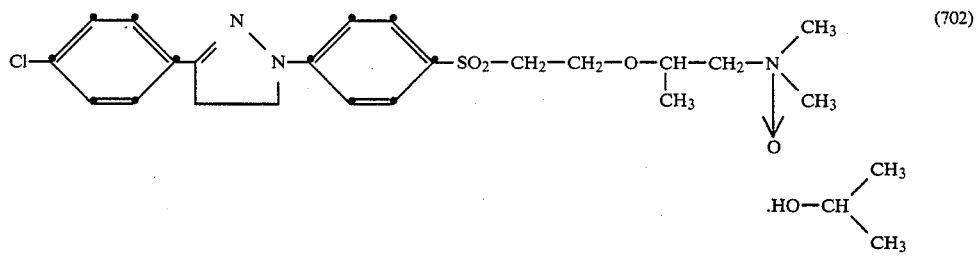
(702)

are obtained in the form of white small needles which melt, with decomposition, at 165° to 170° C. After a further recrystallisation from isopropanol, 10 g of the compound of the formula (702) are obtained in the form of white small needles of melting point 170° to 172° C. (with decomposition).

The preparation of the starting compound of the formula (701) is described in Example 1 of Swiss Patent Specification No. 452,886.

EXAMPLE 8

22 g of the compound of the formula

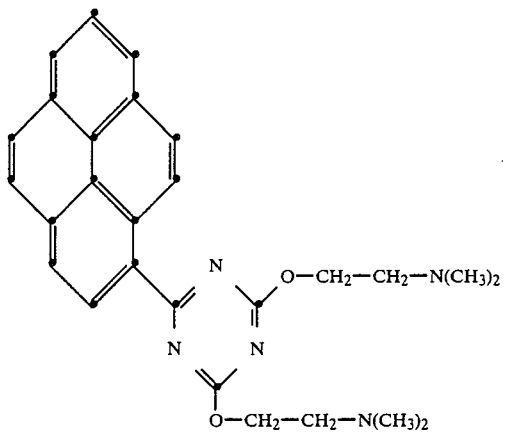
(801)

are dissolved in 250 ml of hot methyl ethyl ketone and 55 ml of 30% hydrogen peroxide are added to the resulting clear solution in the course of 10 minutes, at room temperature. The reaction mixture is stirred for a further 38 hours at room temperature, in the course of which the reaction product slowly precipitates in a crystalline form. It is filtered off and washed with 50 ml of methyl ethyl ketone and dried to constant weight in vacuo at 70° C.

22 g (about 94% of theory) of the compound of the formula

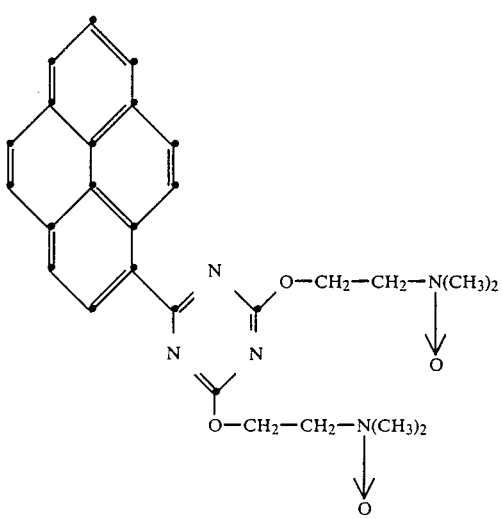
(802)

are obtained in the form of a yellow crystalline powder, which melts, with decomposition, at 152° C. After one recrystallisation from methanol/isopropanol, the compound of the formula (802) is obtained in the form of pale yellow small needles of melting point 156°–158° C. (with decomposition).

The compound of the formula (801), used as the starting material, is prepared as follows:

35 g of the compound of the formula

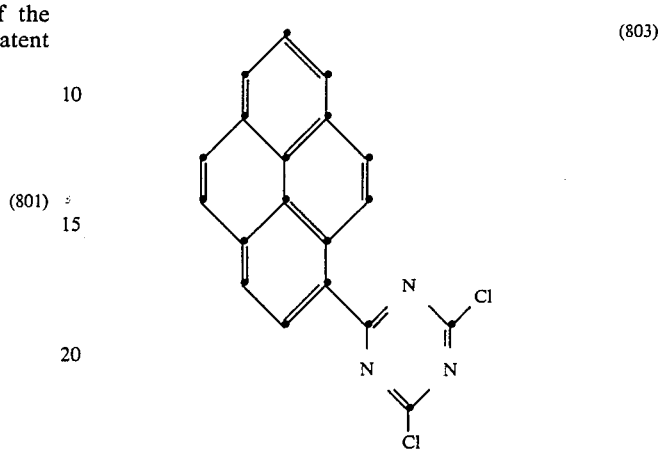
(803)

are suspended in 200 ml of methylene chloride and 4 g of benzyltributylammonium bromide are added. The resulting suspension is cooled to 0° C. and, at this temperature, a solution of 26.8 g of 2-dimethylaminoethanol in 50 ml of methylene chloride is added in the course of 10 minutes, after which 200 ml of a 15% sodium hydroxide solution are added in the course of 20 minutes.

The resuting two-phase reaction mixture is stirred first for one hour at 0° C. and then for 16 hours at room temperature, after which it is diluted with 200 ml of saturated sodium chloride solution. The methylene chloride layer is decanted off, washed with saturated sodium chloride solution until neutral, dried with sodium sulfate and freed from methylene chloride in vacuo.

45 g (about 100% of theory) of the compound of the formula (801) are obtained in the form of a yellow oil. After two recrystallisations from ethyl acetate, with the aid of active charcoal, the compound of the formula (801) is obtained in the form of yellow small needles of melting point 98°–99° C.

The preparation of the starting compound of the formula (803) is described in Example 1 of British Patent Specification No. 985,484.

EXAMPLE 9

A concentrated liquid detergent is prepared by mixing the following components:

|  | % by weight |
|---|---|
| Oxyethylated alcohols ($C_{12}$–$C_{13}$—alcohol with 6.5 mols of ethylene oxide) | 60.0 |
| 1-Methyl-1-oleylamidoethyl-2-oleylimidazolinium methosulfate | 26.7 |
| Compound of the formula (102), (202) or (204) | 0.3 |
| Water | 12.0 |
| Conventional additives | 1.0 |

2 kg of bleached cotton fabric are washed for 10 minutes at 50° C. in 60 liters of water, of 100 ppm hardness, containing 50 to 60 g of the above detergent. After rinsing and drying, the fabric exhibits a strong white effect and a soft handle.

Similar results are obtained if instead of the above detergent, a liquid detergent of the composition

|  | % by weight |
| --- | --- |
| Oxyethylated alcohols ($C_{12}$-$C_{13}$—alcohol with 6.5 mols of ethylene oxide) | 55.0 |
| 1-Methyl-1-talloylamidoethyl-2-tallyl-imidazolinium methosulfate | 26.0 |
| Compound of the formula (102), (202) or (204) | 0.3 |
| Water | 13.0 |
| Isopropanol | 5.0 |
| Conventional additives | 0.7 | or some other liquid detergent containing non-ionic surfactants and cationic substances, for example the commercial products "Perwoll®️ flüssig" or Samtess®️, which contains a brightener according to the invention, of the formula (102), (202) or (204), is used.

Similar good results are obtained if the washing procedure is repeated with one of the abovementioned liquid detergents, which, however, contains the brightener of the formula (103), (104), (203), (302), (402), (502), (503), (602), (702) or (802), in the amounts stated above.

EXAMPLE 10

A liquid detergent is prepared by mixing the following components:

|  | % by weight |
| --- | --- |
| Oxyethylated alcohols ($C_{14}$-$C_{15}$ alcohol with 7 mols of ethylene oxide) | 12.0 |
| Oxyethylated alcohols ($C_{12}$-$C_{13}$ alcohol with 6.5 mols of ethylene oxide) | 12.0 |
| Non-hardened di-tallyl-dimethyl-ammonium chloride | 6.4 |
| Ethanol | 15.0 |
| Sodium bicarbonate | 0.25 |
| Compound of the formula (102), (202) or (204) | 0.41 |
| Conventional additives | 0.41 |
| Water | 53.53 |

Bleached cotton fabric is washed, as described in Example 9, in a liquor which contains the detergent described above. A greatly brightened cotton fabric, having a soft handle, is thereby obtained.

Similar good results are obtained if the washing procedure is repeated with the abovementioned liquid detergent, which, however, contains the brightener of the formula (103), (104), (203), (302), (402), (502), (503), (602), (702) or (802), in the amounts stated above.

EXAMPLE 11

In a dyeing apparatus, a bleached cotton fabric is treated, in a liquor ratio of 1:20, with an aqueous bath which contains 0.1% of a brightener of the formula (102), (103), (104), (202), (203) or (204), relative to the weight of cotton, and also contains 5 g/l of sodium sulfate.

The treatment is carried out in accordance with the following temperature programme:

20°–50° C.: 15 minutes
at 50° C.: 15 minutes

The cotton fabric is then rinsed for 20 seconds in running softened water and is dried in a drying cabinet at 70° C. The cotton fabric thus treated exhibits a good white effect.

EXAMPLE 12

A bleached cotton fabric is padded, at room temperature, with an aqueous liquor which contains 1 g/l of a brightener of the formula (102), (103), (104), (202), (203), (204), (602), (702), (302), (402) or (502). The wet pick-up is 75%.

The fabric is then dried for 30 seconds at 70° C. on a thermofixing apparatus.

The cotton fabric thus treated exhibits a good white effect.

EXAMPLE 13

A polyacrylonitrile fabric (®️Orlon 75) is treated, on a dyeing apparatus, using a liquor ratio of 1:20, with an aqueous bath which contains 0.1% of a brightener of the formula (102), (202), (203), (204), (302), (402), (502), (503) or (702), relative to the weight of the fabric, 1 g/l of an adduct of 35 mols of ethylene oxide with 1 mol of stearyl alcohol and 1.5 ml/l of 85% formic acid.

The treatment is carried out in accordance with the following temperature programme:

40°–97° C.: 30 minutes
at 97° C.: 30 minutes
97°–40° C.: 15 minutes.

The polyacrylonitrile fabric is then rinsed for 20 seconds in running softened water and is dried in a drying cabinet at 70° C. The fabric thus treated exhibits a good white effect.

EXAMPLE 14

A bleached cotton fabric is treated for 15 minutes, using a liquor ratio of 1:20, in an aqueous soft-rinse liquor, at 30° C., which contains 0.2 g of dimethyldistearylammonium chloride and 0.01 g of a brightener of the formula (102), (103), (104), (202), (203), (204) or (602) per liter.

The cotton fabric is then rinsed for 5 seconds in running water and is dried in a drying cabinet at 70° C. The cotton fabric thus treated exhibits a good white effect.

EXAMPLE 15

A bleached cotton fabric is washed for 15 minutes, using a liquor ratio of 1:20, in an aqueous liquor, at 40° C., which contains 0.5 g of an adduct of 10 mols of ethylene oxide to one mol of stearyl alcohol and 0.01 g of a brightener of the formula (102), (103), (104), (202), (203), (204) or (802) per liter.

The cotton fabric is then rinsed for 20 seconds in running water and is dried in a drying cabinet at 70° C. The cotton fabric thus treated exhibits a good white effect.

EXAMPLE 16

A modified polyacrylonitrile fabric (Courtelle®️) is treated, on a dyeing apparatus, using a liquor ratio of 1:20, with an aqueous bath which contains 0.1% of a brightener of the formula (102), (202), (203), (204), (302), (402), (502), (503) or (702), relative to the weight of the fabric, 1 g/l of oxalic acid, 0.25 g/l of a polyphosphate as a complexing agent and 0.125 g/l of sodium metabisulfite. The treatment is carried out in accordance with the following temperature programme:

40°–97° C.: 30 minutes
at 97° C.: 30 minutes
97°–40° C.: 15 minutes

The polyacrylonitrile fabric is then rinsed for 30 seconds in running softened water and is dried in a drying cabinet at 70° C. The fabric thus treated exhibits a good white effect.

EXAMPLE 17

A polyamide-6 fabric is treated, on a dyeing apparatus, using a liquor ratio of 1:20, with an aqueous bath which contains 0.3% of a brightener of the formula (102), (103), (104), (202), (203), (204), (302), (602) or (802), relative to the weight of the fabric, 1 g/l of an adduct of 35 mols of ethylene oxide to 1 mol of stearyl alcohol, 1 g/l of an adduct of 8 mols of ethylene oxide to 1 mol of p-tert.-octylphenol and 0.5 g/l of sodium phosphate buffer. The treatment is carried out in accordance with the following temperature programme:
50°–100° C. in the course of 10 minutes,
100° C. for 20 minutes
100°–50° C. in the course of 5 minutes.
The fabric is then rinsed in softened cold water and dried at 60° C. The fabric thus treated exhibits a good white effect.

EXAMPLE 18

A polyamide-6 fabric is treated, on a dyeing apparatus, using a liquor ratio of 1:20, with an aqueous bath which contains 0.3% of a brightener of the formula (102), (103), (202), (204), (302) or (602), relative to the weight of the fabric, 1 g/l of an adduct of 35 mols of ethylene oxide to 1 mol of stearyl alcohol, 1 g/l of an adduct of 8 mols of ethylene oxide to 1 mol of p-tert.-octylphenol and 0.5 g/l of sodium phosphate buffer. The treatment is carried out in accordance with the following temperature programme:
30°–60° C. in the course of 10 minutes,
at 60° C. for 20 minutes.
The fabric is then rinsed in softened cold water and dried at 60° C. The fabric thus treated exhibits a good white effect.

EXAMPLE 19

5 g of fibrous material (consisting of bleached sulfite cellulose and bleached beech cellulose in the ratio of 1:1) in 50 ml of water are mixed for 15 minutes, in a mixer, with 150 ml of brightener solution, containing 2.5 mg (corresponding to a concentration of 0.05%) of a brightener of the formula (702) or (802). 1.5% by weight of size, for example Bewoidleim ®, and 2.5% by weight of aluminium sulfate (relative to the dry fibre weight) are added and the mixture is diluted to 1,000 ml with water of about 10° German hardness. A paper sheet showing a good white effect is produced from this fibre suspension.

EXAMPLE 20

5 g of fibrous material (consisting of bleached sulfite cellulose and bleached beech cellulose in the ratio of 1:1) in 150 ml of water containing 5 mg of a cationic polyether-amine are mixed for 15 minutes, in a mixer, with 50 ml of brightener solution, containing 2.5 mg (corresponding to a concentration of 0.05%) of a brightener of the formula (502) or (802). 1.5% by weight of size, for example Bewoidleim ®, and 2.5% by weight of aluminium sulfate and 0.1% of a cationic polyether-amine (relative to the dry fibre weight) are added and the mixture is diluted to 1,000 ml with water of about 10° German hardness. A paper sheet showing a good white effect is produced from this fibre suspension.

EXAMPLE 21

5 g of fibrous material (consisting of bleached sulfite cellulose and bleached beech cellulose in the ratio of 1:1) in 150 ml of water containing 5 mg of a polethyleneimine are mixed for 15 minutes, in a mixer, with 50 ml of brightener solution, containing 2.5 mg (corresponding to a concentration of 0.05%) of a brightener of the formula (702) or (802). 1.5% by weight of size, for example Bewoidleim ®, and 2.5% by weight of aluminium sulfate and 0.1% of a polyethyleneimine (relative to the dry fibre weight) are added and the mixture is diluted to 1,000 ml with water of about 10° German hardness. A paper sheet showing a good white effect is produced from this fibre suspension.

EXAMPLE 22

An intimate mixture of 100 parts of polyvinyl chloride, 3 parts of stabiliser (Advastab BD 100 ®; Ba/Cd complex), 2 parts of titanium dioxide, 59 parts of dioctyl phthalate and 0.01 to 0.2 part of a brightener of the formula (802) is milled on a calendering machine at 150° to 155° C. to give a sheet. The opaque polyvinyl chloride sheet thus obtained has a substantially greater whiteness than a sheet which does not contain the fluorescent brightener.

What is claimed is:

1. An amine oxide compound of the formula

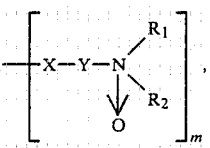

in which m is 1 or 2, A is a brightener radical selected from the group consisting of the 4,4′-distyrylbiphenyls, 4,4′-divinyl-stilbenes and 1,4-distyrylbenzenes, which are unsubstituted or substituted by 1-4 substituents selected from halogen, alkyl, hydroxyalkyl, halogenoalkyl, cyanoalkyl, alkoxyalkyl, phenylalkyl, carboxyalkyl, carbalkoxyalkyl, alkenyl, cycloalkyl, alkoxy, alkenyloxy, alkoxycarbonyl, carbamoyl, cyano, alkylsulfonyl, phenylsulfonyl, alkyloxysulfonyl, sulfamoyl, hydroxyl, carboxyl, sulfo and trifluoromethyl, X is a direct bond between A and Y, an oxygen atom or sulfur atom or a group of the formula $-SO_2-$, $-SO_2-O-$, $-COO-$, $-CON(R)-$ or $-SO_2N(R)-$, in which R is hydrogen, alkyl or alkyl substituted by halogen, cyano, hydroxyl, $C_2-C_5$-carbalkoxy, $C_1-C_4$-alkoxy, phenyl, chlorophenyl, methylphenyl, methoxyphenyl, carbamoyl or sulfamoyl, Y is alkylene or alkyleneoxyalkylene or either of said groups substituted by halogen, hydroxyl, $C_2-C_5$-carbalkoxy, $C_1-C_4$-alkoxy, phenyl, chlorophenyl, methylphenyl, methoxyphenyl, carbamoyl or sulfamoyl, and $R_1$ and $R_2$ independently of one another are cycloalkyl, alkyl or phenyl, or alkyl substituted by halogen, hydroxy, $C_2-C_5$-carbalkoxy, $C_1-C_4$-alkoxy, phenyl, chlorophenyl, methylphenyl, methoxyphenyl, carbamoyl or sulfamoyl, wherein in all said carbamoyl or sulfamoyl groups the nitrogen atom is unsubstituted or substituted by 1 or 2 groups chosen from $C_1-C_4$-alkyl, $C_1-C_4$-hydroxyalkyl, $C_2-C_5$-cyanoalkyl, $C_1-C_4$-halogenalkyl, benzyl or phenyl.

2. An amine oxide compound of claim 1 of the formula

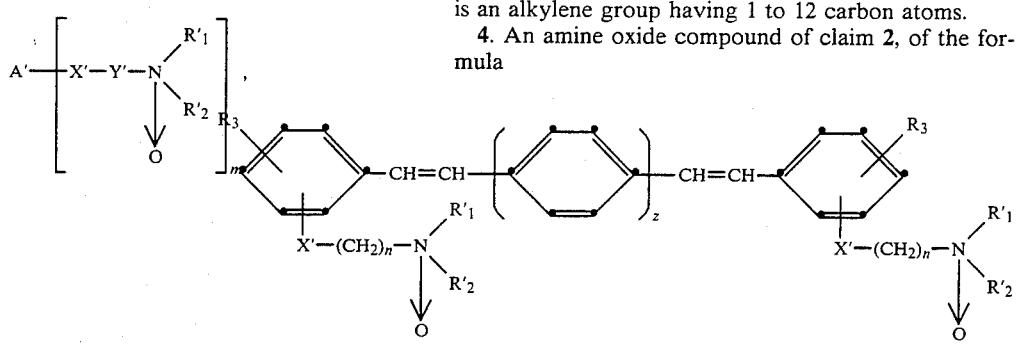

in which A' is of the formula

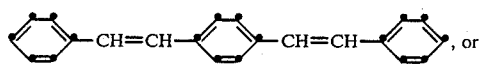, or

unsubstituted or substituted as in claim 1, X' is an oxygen atom or a group of the formula —SO₂N(R')— or —SO₂—, R' being hydrogen or alkyl, having 1 to 4 carbon atoms, which is unsubstituted or substituted by hydroxyl, cyano or halogen, Y' is an alkylene or alkyleneoxyalkylene group, m is 1 or 2 and $R_1'$ and $R_2'$ independently of one another are alkyl having 1 to 8 carbon atoms, which is unsubstituted or substituted by halogen, cyano, hydroxyl, alkoxy having 1 to 4 carbon atoms, phenyl, chlorophenyl, methoxyphenyl, methylphenyl or alkoxycarbonyl having 2 to 5 carbon atoms.

3. An amine oxide compound of claim 1, in which X is an oxygen atom or sulfur atom or a group of the formula —SO₂—, —CON(R)— or —SO₂N(R)— and Y is an alkylene group having 1 to 12 carbon atoms.

4. An amine oxide compound of claim 2, of the formula

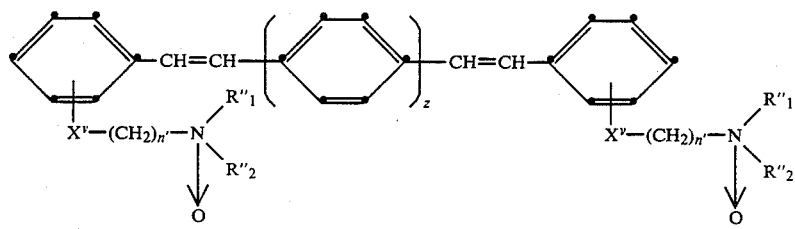

in which z is the integer 1 or 2 and n is an integer between 1 and 4, X', $R_1'$ and $R_2'$ are defined as in claim 2 and $R_3$ is halogen, alkyl having 1 to 4 carbon atoms, cycloalkyl having 5 or 6 carbon atoms, alkoxy having 1 to 4 carbon atoms, alkylsulfonyl having 1 to 4 carbon atoms, phenylsulfonyl, carbalkoxy having 2 to 5 carbon atoms, carbamoyl or sulfamoyl.

5. An amine oxide compound of claim 2, of the formula

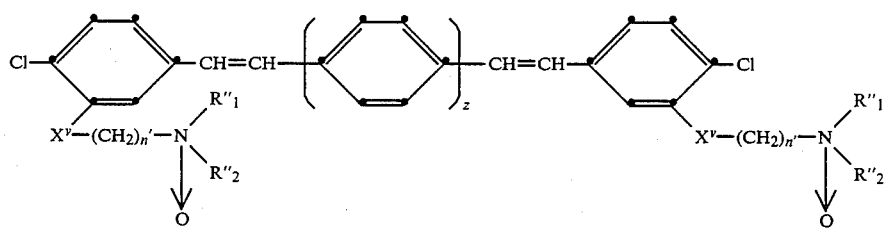

in which z is the integer 1 or 2, $X^v$ is an oxygen atom or a group of the formula —SO₂N(R')—, R' being hydrogen or alkyl which has 1 to 4 carbon atoms and is unsubstituted or substituted by hydroxyl, cyano or halogen, n' is an integer between 1 and 3 and $R_1''$ and $R_2''$ independently of one another are alkyl or hydroxyalkyl having 1 to 4 carbon atoms.

6. An amine oxide compound of claim 4, of the formula in which z is the integer 1 or 2, $X^v$ is an oxygen atom or a group of the formula —SO₂N(R'), R' being hydrogen or alkyl which has 1 to 4 carbon atoms and is unsubstituted or substituted by hydroxyl, cyano or halogen, n' is an integer between 1 and 3 and $R_1''$ and $R_2''$ independently of one another are alkyl or hydroxyalkyl having 1 to 4 carbon atoms.

* * * * *